United States Patent
Schnell et al.

(10) Patent No.: US 7,150,798 B2
(45) Date of Patent: Dec. 19, 2006

(54) NON-DESTRUCTIVE TESTING METHOD OF DETERMINING THE SERVICE METAL TEMPERATURE OF A COMPONENT

(75) Inventors: Alexander Schnell, Ennetbaden (CH); Giampiero Antonelli, Monza (IT); Klaus Germerdonk, Ennetbaden (CH)

(73) Assignee: Alstom Technology Ltd., Baden (CH)

( * ) Notice: Subject to any disclaimer, the term of this patent is extended or adjusted under 35 U.S.C. 154(b) by 0 days.

(21) Appl. No.: 10/726,608

(22) Filed: Dec. 4, 2003

(65) Prior Publication Data

US 2004/0159376 A1   Aug. 19, 2004

(30) Foreign Application Priority Data

Dec. 6, 2002   (EP)   ................................. 02406064

(51) Int. Cl.
 *C21D 1/55* (2006.01)
 *C21D 11/00* (2006.01)
(52) U.S. Cl. ...................... 148/509; 148/508; 324/233
(58) Field of Classification Search ............... 148/508, 148/509; 324/233
See application file for complete search history.

(56) References Cited

U.S. PATENT DOCUMENTS

| | | |
|---|---|---|
| 3,528,861 A | 9/1970 | Elam et al. |
| 3,676,085 A | 7/1972 | Evans et al. |
| 3,754,903 A | 8/1973 | Goward et al. |
| 4,152,223 A | 5/1979 | Wallace et al. |
| 4,313,760 A | 2/1982 | Dardi et al. |
| 4,346,137 A | 8/1982 | Hecht |
| 4,419,416 A | 12/1983 | Gupta et al. |
| RE32,121 E | 4/1986 | Gupta et al. |
| 4,585,481 A | 4/1986 | Gupta et al. |
| 4,643,782 A | 2/1987 | Harris et al. |
| 4,743,514 A | 5/1988 | Strangman et al. |
| 4,973,445 A | 11/1990 | Singheiser |
| 5,430,376 A | 7/1995 | Viertl |
| 5,759,301 A | 6/1998 | Konter et al. |
| 5,888,451 A | 3/1999 | Konter et al. |
| 6,201,391 B1 | 3/2001 | Burkhardt et al. |
| 6,534,975 B1 * | 3/2003 | Beeck et al. ................. 324/230 |
| 2004/0082069 A1* | 4/2004 | Jiang et al. ..................... 436/2 |

FOREIGN PATENT DOCUMENTS

| | | |
|---|---|---|
| DE | 3740478 C1 | 1/1989 |
| EP | 1052505 A1 | 11/2000 |

OTHER PUBLICATIONS

"Non-Destructive Condition Assessment of Serviced MCrAlY Coatings", Giampiero Antonelli, CESI, Milan. Italy, Dec. 2002, pp. 1-12.
"Qualification of a Frequency Scanning Eddy Current Equipment for Nondestructive Characterization of new and Serviced High-Temperature Coatings", Antonelli, et al., Proceedings of ASME Turbo Expo 2001, Jun. 4-7, 2001, New Orleans, Louisiana, USA, pp. 1-8.

* cited by examiner

*Primary Examiner*—Scott Kastler
(74) *Attorney, Agent, or Firm*—Buchanan Ingersoll & Rooney PC

(57) ABSTRACT

It is disclosed a method of determining the exposure temperature of Al and Cr of a $\gamma/\gamma'$ MCrAlY-coating after the use in a high temperature environment, the $\gamma/\gamma'$ MCrAlY-coating exhibiting a non-equilibrium $\gamma/\gamma'$-microstructure at a temperature lower than the temperature during operation and the depletion of chromium from the $\gamma/\gamma'$-MCrAlY-coating still allows the $\alpha$-Cr phase to form. The coating conductivity and permeability by means of a multifrequency eddy current system is measured at different locations of the component and from the measured conductivity and permeability the exposure temperature of said different locations of the components is determined.

12 Claims, 3 Drawing Sheets

NON-DESTRUCTIVE TESTING METHOD OF DETERMINING THE SERVICE METAL TEMPERATURE OF A COMPONENT

FIELD OF INVENTION

The invention relates to a method of non-destructively testing a component after exposure in a high temperature environment.

STATE OF THE ART

Components designed for the use in the area of high temperature, e.g. blades or vanes of a gas turbine, are usually coated with resistant coatings. The coating protects the base material against corrosion and oxidation due to the thermal effect of the hot environment and consists of an alloy mostly using the elements Al and Cr. Most turbine components are coated for the protection from oxidation and/or corrosion with, for example, a MCrAlY coating (overlay coating) and some are also coated with a thermal barrier coating (TBC) for thermal insulation. MCrAlY protective overlay coatings are widely known in the prior art. They are a family of high temperature coatings, wherein M is selected from one or a combination of iron, nickel and cobalt. As an example U.S. Pat. No. 3,528,861 or U.S. Pat. No. 4,585,481 are disclosing such kind of oxidation resistant coatings. U.S. Pat. No. 4,152,223 as well discloses such method of coating and the coating itself. Besides the γ/β-MCrAlY-coating, there is another class of overlay MCrAlY coatings which are based on a γ/γ'-gamma/gamma prime-structure. The advantages of γ/γ'-coatings over γ/β-coatings is that they have a negligible thermal expansion mismatch with Nickel-based superalloy of the underlying turbine article.

Among γ/γ'-coatings and γ/β-coatings, the field of γ/β-coatings have been an active area of research and a series of patents has been issued. E.g. a NiCrAlY coating is described in U.S. Pat. No. 3,754,903 and a CoCrAlY coating in U.S. Pat. No. 3,676,085. U.S. Pat. No. 4,346,137 discloses an improved high temperature fatigue resistance NiCoCrAlY coating. U.S. Pat. No. 4,419,416, U.S. Pat. No. 4,585,481, RE-32,121 and U.S. Pat. No. 4,743,514 describe MCrAlY coatings containing Si and Hf. U.S. Pat. No. 4,313,760 discloses a superalloy coating composition with good oxidation, corrosion and fatigue resistance.

In contrast to the γ/β-coatings, the γ/γ'-type of MCrAlY coatings, known e.g. from U.S. Pat. No. 4,973,445, are relatively new. The unique feature of this type of γ/γ'-coatings is that their thermal expansion mismatch is close to zero in combination with a high ductility, what make these coatings more resistant to thermal fatigue. However the limitations at elevated temperature are the lower aluminum content compared to γ/β-coatings.

For coated gas turbine blading components the in-service degradation of the protective coating is one of the key factors for setting the time schedule for the periodic maintenance of gas turbines. In this context quantitative non-destructive characterization of high-temperature coating is an arising interest both to assess the quantity (thickness) of the coating in the "as applied" condition and to obtain objective and reliability data on coating operational degradation that can be used to optimize blade refurbishment cycles.

To determine the condition of serviced gas turbine blading components many components need to be metallurgically investigated because the of the main question of coating degradation. Non-destructive Testing (NDT) methods can provide essential information, such as residual coating lifetime, coating thickness distribution and presence and size of any kind of delamination defects. Therefore, NDT methods lower the need of time and cost consuming destructive metallurgical investigations. Within the family of the NDT methods, advanced multifrequency eddy current techniques can be used to quantitatively grade the expended life of service exposed MCrAlY coatings having γ/βmicrostructure. This technique exploits the correlation between the coating chemical composition, which changes in operation due to the loss of protective elements, and the electromagnetic properties of the coating, i.e. electrical conductivity and magnetic permeability, which are estimated by the eddy current technique. However, unlike for γ/βcoatings, the applicability of NDT eddy current methods for estimating the expended life of service exposed γ/γ' coatings is not straightforward due to the variability of the γ/γ' microstructure and strong dependence of the γ/γ'-coating electrical conductivity on the service temperature.

During an engine stop from the operating temperature down to below 600°, the γ/γ' MCrAlY-coating exhibits a non-equilibrium γ/γ'-microstructure at room temperature. Due to the rapid cooling of the component in the engine the equilibrium phases, which are stable at low temperatures such as the α-Chromium phase, can not re-precipitate. The non-equilibrium microstructure of the coating results in a modified coating conductivity compared to the equilibrium microstructure according to the standard heat treatment. This variation superposes to the conductivity change due to coating depletion, i.e. the loss of protective elements, which is the important piece of information for determining the expended life of the coating. Therefore the conductivity dependence on coating microstructure makes an NDT coating assessment using the multifrequency eddy current method unreliable for γ/γ' MCrAlY-coatings.

SUMMARY OF THE INVENTION

It is object of the present invention to find a method of non-destructively determining the service metal temperature of γ/γ'-GT blading components at different locations after the use in a high temperature environment.

According to the invention a method of determining the service metal temperature of a γ/γ' MCrAlY-coated component after the use in a high temperature environment was found, the γ/γ' MCrAlY-coating applied to the component exhibits a non-equilibrium γ/γ'-microstructure at a temperature lower than the temperature during operation and the depletion of chromium from the γ/γ'-MCrAlY-coating still allows the α-Cr phase to form. The inventive method comprising the steps of
(a) measuring the coating electrical conductivity and magnetic permeability of the MCrAlY-coating at different locations of the components by means of a multi-frequency eddy current system and
(b) determining the exposure temperature of said different locations of the components from the measured conductivity and permeability.

Such coating of serviced gas turbine blading components can consist of (wt.-%) 25% Cr, 5.5% Al, 1% Ta, 2.6% Si, 0.5%Y, rest Ni and unavoidable impurities.

BRIEF DESCRIPTION OF DRAWINGS

This invention is illustrated in the accompanying drawing, in which.

The drawings show only parts important for the invention.

DETAILED DESCRIPTION OF INVENTION

Figure 1:
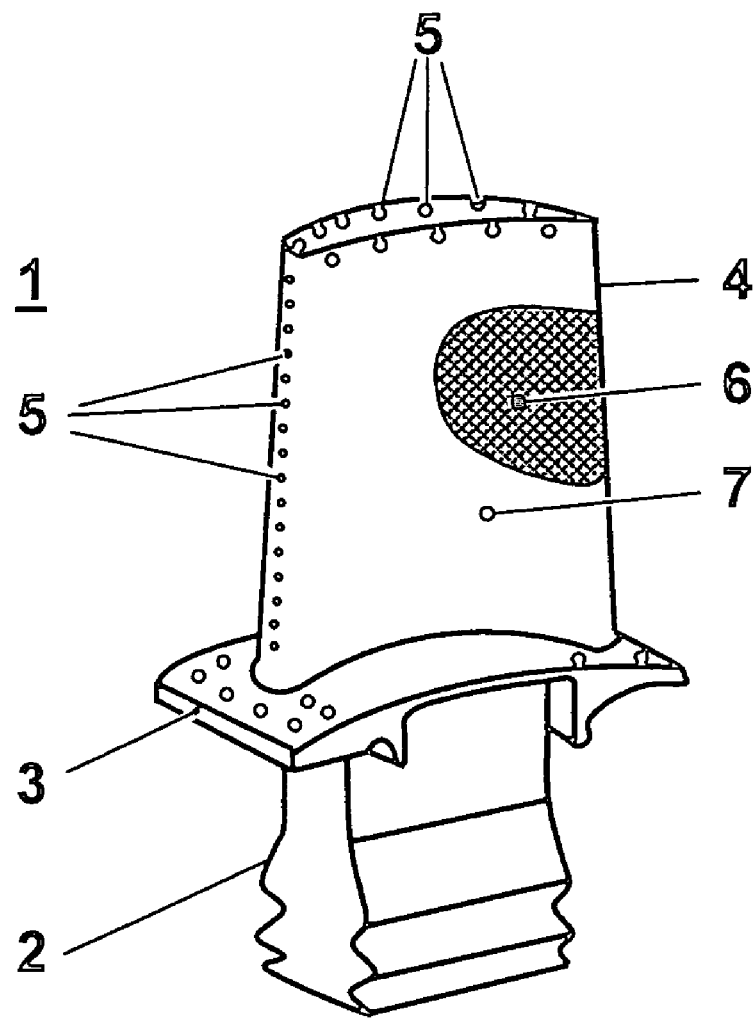
FIG. 1 shows a turbine blade.

As an example FIG. 1 shows an article 1 such as blades or vanes of gas turbine engines, the gas turbine blade comprising a root portion 2, a platform 3 and a blade 4 and cooling holes 5. On the external surface 7 a MCrAlY-coating 6 is applied. The component can be made from a Nickel base superalloy known in the state of the art, e.g. from the document U.S. Pat. No. 5,888,451, U.S. Pat. No. 5,759,301 or from U.S. Pat. No. 4,643,782, which is known as "CMSX-4".

The invention relates to a method for determining the exposure temperature of $\gamma/\gamma'$ MCrAlY-coatings 6—e.g. like SV20 coating—after the use of this component in a high temperature environment.

The chemical composition (wt.-%) of the SV20-MCrAlY coating, which is known from DE-C1-37 40 478 or U.S. Pat. No. 4,973,445, is shown in Table 1:

TABLE 1

| Coating | Ni | Cr | Al | Ta | Si | Y |
|---|---|---|---|---|---|---|
| SV20 | Balance | 25 | 5.5 | 1 | 2.6 | 0.5 |

After the standard heat treatment (1120° C./2 h+870/20 h) the SV20 coating shows a microstructure consisting of a $\gamma$-Ni-matrix with the Al rich $\gamma'$ phase and Cr-rich $\alpha$-Cr phase. The equilibrium volume fraction of the $\alpha$-Cr phase in the initial state SV20 is approximately 20%. The $\gamma'$ phase is the Al reservoir phase for the formation of alumina to protect against high temperature oxidation above 900° C. The $\alpha$-Cr phase is the Cr reservoir phase for the formation of Cr-Oxide to protect against low temperature oxidation and corrosion.

Unlike a MCrAlY with a $\gamma/\beta$-structure, which is stable on a wide temperature range, the microstructure of the non-depleted SV20 coating is strongly dependent on the temperature the component is subjected to during operation. Besides the microstructural changes in the non-depleted SV20 coating as a function of the operating temperature also the oxidation and outer depletion behaviour of the SV20 changes with temperature.

At temperatures between 750° and 900° C. the SV20 coating consists of the $\gamma$-Ni-matrix, the $\gamma'$ and the $\alpha$-Cr phases. The SV20 coating does not show a significant microstructural change during cooling from temperatures below 850° C. down to Room temperature (RT). Mainly chromium-oxide forms at the outer surface of the SV20 coating which leads to a chromium depleted layer in the SV20 coating. The degradation level of the SV20 coating can be metallographically investigated by measuring the loss of $\alpha$-Cr phase in the coating. The coating is considered exhausted (conservative approach) when a Cr content lower than 12–15 wt % is reached.

At temperatures above 900° C. the $\alpha$-Cr phase starts to dissolve and with increasing temperature and time the fraction of the $\alpha$-Cr phase decreases permanently until the $\alpha$-Cr phase is completely dissolved. The cooling rates during an engine stop are generally too high for a re-precipitation of the $\alpha$-Cr phase. This means that the microstructure of a SV20 coating, which was subjected to temperatures higher than 900° C., shows a lower $\alpha$-Cr phase content compared to its equilibrium condition. The SV20 coating depletes at this temperature mainly from Al as the SV20 coating forms Al-oxides as the protective oxide scale. The degradation level of the SV20 coating above 900° C. can be metallographically investigated by measuring the thickness of the $\gamma'$ free layer. The coating is considered exhausted when an Al content lower than 3 wt % is reached.

At elevated temperatures of above 1000° C. a phase transformation according to $\alpha+\gamma' \leftrightarrow \beta+\gamma$ takes place. The $\alpha$-Cr phase is entirely dissolved and the $\gamma$ and Al-rich $\beta$ phase are in an equilibrium condition. During an engine stop the cooling rates are generally too high for a complete re-transformation to the equilibrium microstructure at RT. Such SV20 coatings, which were subjected to temperatures above 1000° C. in service, show a non-equilibrium microstructure at RT consisting of all four phases: $\alpha+\gamma'+\beta+\gamma$.

Figure 2:
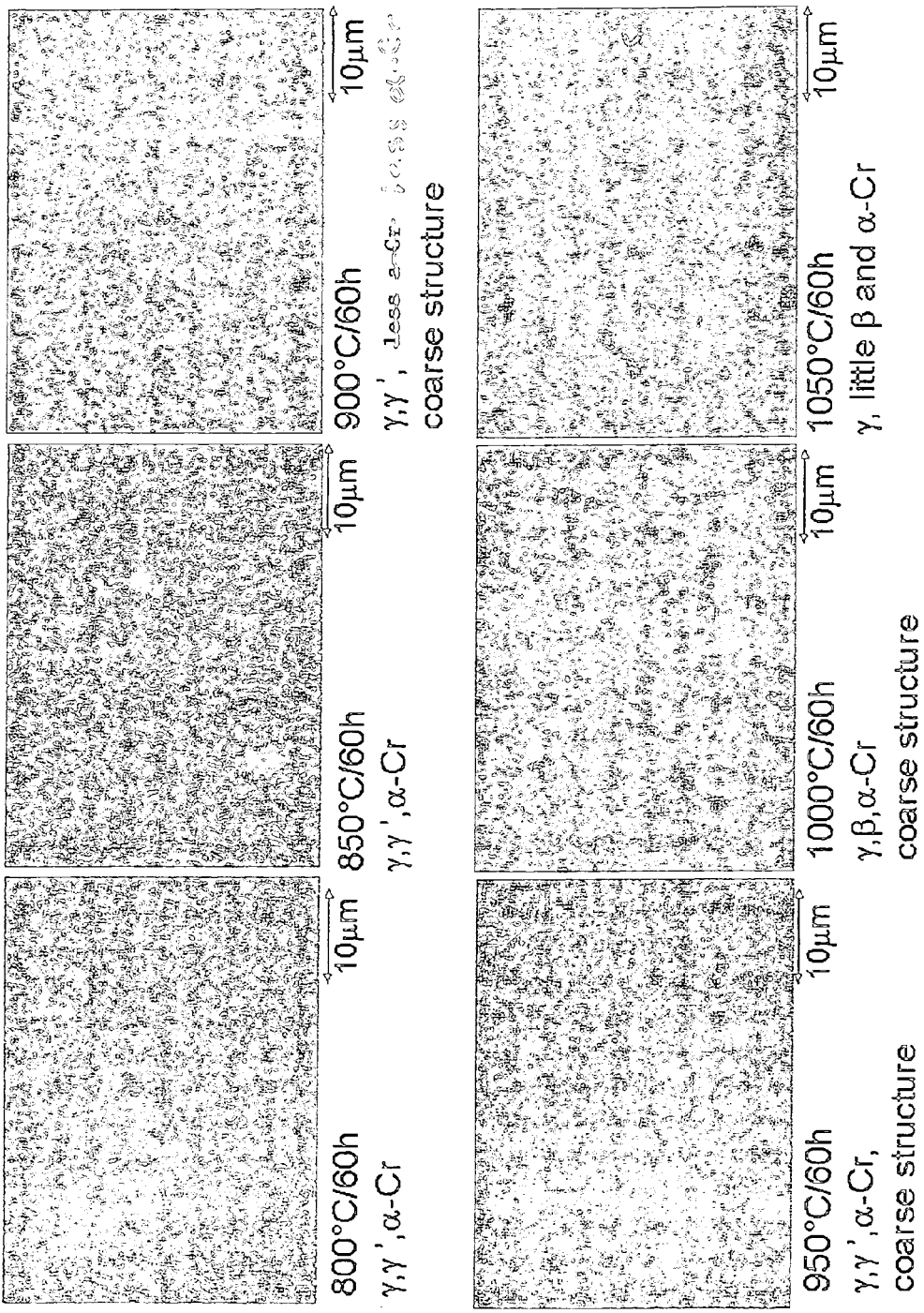
FIG. 2 shows the coating structure after exposure with rapid cooling afterwards resulting in non-equilibrium microstructure.

In order to assess the influence of the presence, fraction and size of the $\alpha$, $\gamma'$, $\beta$ phases in the $\gamma$-matrix on the electrical conductivity and magnetic permeability of the SV20 coating, tests were performed on the following sets of samples:

6 samples of "as applied" SV20/MarM247 (subjected to the standard heat treatment at 1120° C./2 h+870° C./20 h) were annealed for 60 hours at the following temperatures: 800° C., 850° C., 900° C., 950° C., 1000° C. and 1050° C. All samples were then quenched in air resulting in high cooling rates in order to maintain the non-equilibrium $\gamma/\gamma'$-microstructure at room temperature. FIG. 2 shows the structure of the coating after exposure to above mentioned heat treatments.

The set of SV20 samples were measured before and after the long-term exposure at several temperatures using a multifrequency eddy current system as described as an example in Antonelli, G., Crisafulli, P., Tirone, G., 2001, "Qualification of a Frequency Scanning Eddy Current Equipment for Nondestructive Characterization of New and Serviced High-Temperature Coatings", ASME paper No. 2001-GT-0419 and Antonelli, G., 2002, "Non-Destructive Condition Assessment of MCrAlY Coatings", presented at Turbine Forum on Advanced Coatings for High Temperatures, Nice, France. This system was developed for non-destructive condition assessment of new and service exposed high-temperature coatings applied on the hot gas-path components of land-based gas turbines.

Figure 3:
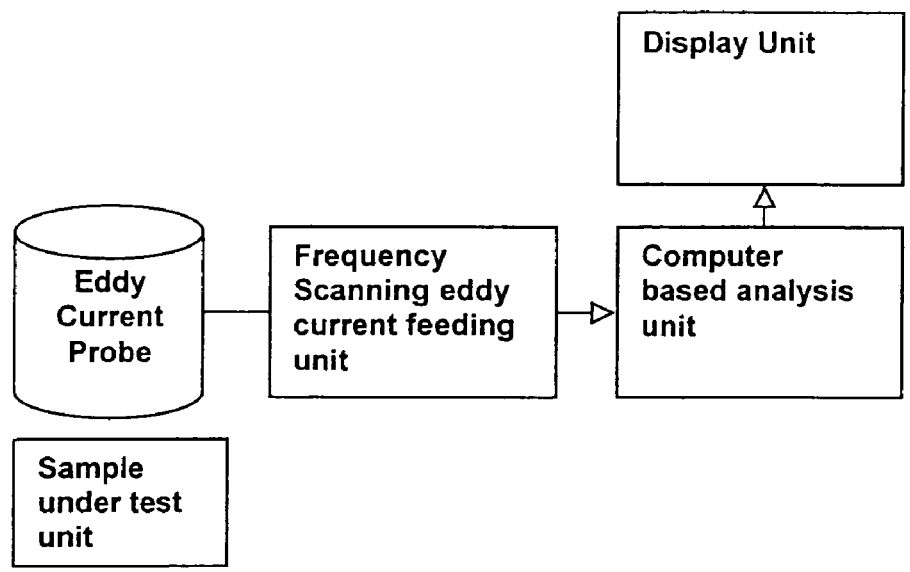
FIG. 3 illustrates a schematic drawing of a multifrequency eddy current system and FIG. 4 shows a diagram explaining that the temperature profile through a gas turbine blading component consisting of the ceramic coating and bondcoat.

A schematic view of the system is given in FIG. 3. It is a portable system consisting of following modules:

Probe with combined or separated transmit-receiver coils,
Eddy current frequency scanning range from 100 kHz to 10 MHz,
Feeding and conditioning unit with high sensitivity and high stability,
Computer based data analysis unit and
Display unit The system fully exploits the capabilities of multiple-frequency eddy current techniques in the characterisation of multiple-layer materials, based on the evaluation of even quite small differences in the electrical conductivity values of the different layers.

The influence of the non-equilibrium microstructure from the coatings aged above 900° C. on the eddy current data is significant. Those coatings seem to be heavily depleted and degraded due their non-equilibrium structure. With increasing ageing temperature the fraction of the $\alpha$-Cr phase decreases permanently which results in a lower normalised impedance curve obtained by the frequency scanning eddy current system. At temp. >950° C. the $\beta$ phase occurs which then results again in an increase of the normalised impedance curve. The normalised impedance curve for the 950° C.-exposed sample is the lowest.

The above qualitative analysis of the impedance curves is confirmed by model based analysis of the impedance curves giving estimates for coating and substrate conductivity. There is a strong dependence of the coating conductivity on the exposure temperature as estimated by the frequency scanning eddy current system, especially in the range from 800° C. to 950° C., where electrical conductivity correlates well with Cr dissolution. This effect poses a problem in the interpretation of eddy current data from service exposed blades. The coating conductivity depends on two effects, of which only the first is related with real coating consumption:
Cr-depletion as a consequence of coating oxidation (depletion effect);
α-Cr dissolution as a consequence of non-equilibrium microstructures obtained at different operating temperatures (microstructural effect).

Figure 4:
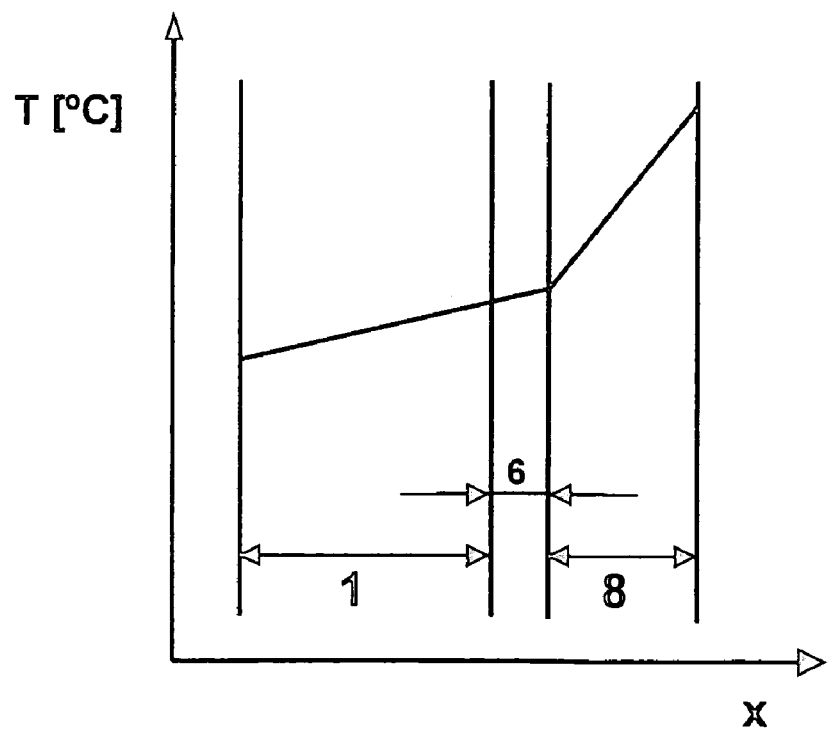

FIG. 4 shows a diagram explaining the temperature profile through a gas turbine blading component consisting of the ceramic coating 8 and bondcoat 6 having a distance x. FIG. 4 shows that the temperature of the bondcoat 6 reflects the outer base metal temperature of the article 1 which is actually the temperature of main interest according to the present invention. The determination on the exposure temperature can be performed if the depletion of chromium from the γ/γ'-MCrAlY-coating still allows the α-Cr phase to form.

While our invention has been described by an example, it is apparent that other forms could be adopted by one skilled in the art. Accordingly, the scope of our invention is to be limited only by the attached claims.

REFERENCE LIST

1 Article
2 Root portion
3 Platform
4 Blade
5 Cooling holes
6 Coating
7 External surface of article 1
8 Ceramic coating
x Distance

The invention claimed is:

1. A method of determining the service metal temperature of a γ/γ' MCrAlY-coated component after use of the component in a high temperature environment, where the γ/γ'-MCrAlY-coating of the component exhibits a non-equilibrium γ/γ'-microstructure at a temperature lower than the temperature during operation and the depletion of chromium from the γ/γ'-MCrAlY-coating still allows the α-Cr phase to form, the method comprising:
(a) measuring qualitatively impedance curves or measuring the coating electrical conductivity and magnetic permeability of the non-equilibrium MCrAlY-coating of the component in the post-service condition at different locations of the component by means of a multi-frequency eddy current system;
(b) then subjecting the coated component to a heat treatment to transform the non-equilibrium MCrAlY coating into an equilibrium microstructure of the coating;
(c) then measuring qualitatively impedance curves or measuring the electrical conductivity and magnetic permeability of the equilibrium MCrAlY-coating at different locations of the component by means of a multi-frequency eddy current system; and
(d) determining the exposure temperature of the different locations of the component based on the difference in the measured impedance curves or the measured conductivities and permeabilities, before and after the heat treatment according to (b).

2. The method according to claim 1, wherein the coating consists of (wt.-%) 25% Cr, 5.5% Al, 1% Ta, 2.6% Si, 0.5% Y, rest Ni and unavoidable impurities.

3. The method according to claim 1, which comprises determining the service metal temperature of a gas turbine blade.

4. The method according to claim 2, which comprises determining the service metal temperature of a gas turbine blade.

5. The method according to claim 1, wherein:
(a) comprises measuring qualitatively impedance curves of the non-equilibrium MCrAlY-coating of the component in the post-service condition at the different locations of the component;
(c) comprises measuring qualitatively impedance curves of the equilibrium MCrAlY-coating at the different locations of the component; and
(d) comprises determining the exposure temperature of the different locations of the component based on the difference in the measured impedance curves, before and after the heat treatment according to (b).

6. The method according to claim 5, wherein the coating consists of (wt.-%) 25% Cr, 5.5% Al, 1% Ta, 2.6% Si, 0.5% Y, rest Ni and unavoidable impurities.

7. The method according to claim 6, which comprises determining the service metal temperature of a gas turbine blade.

8. The method according to claim 5, which comprises determining the service metal temperature of a gas turbine blade.

9. The method according to claim 1, wherein:
(a) comprises measuring the coating electrical conductivity and magnetic permeability of the non-equilibrium MCrAlY-coating of the component in the post-service condition at the different locations of the component;
(c) comprises measuring the coating electrical conductivity and magnetic permeability of the equilibrium MCrAlY-coating at the different locations of the component; and
(d) comprises determining the exposure temperature of the different locations of the component based on the difference in the measured conductivities and permeabilities, before and after the heat treatment according to (b).

10. The method according to claim 9, wherein the coating consists of (wt.-%) 25% Cr, 5.5% Al, 1% Ta, 2.6% Si, 0.5% Y, rest Ni and unavoidable impurities.

11. The method according to claim 10, which comprises determining the service metal temperature of a gas turbine blade.

12. The method according to claim 9, which comprises determining the service metal temperature of a gas turbine blade.

* * * * *